(12) United States Patent
Appleby et al.

(10) Patent No.: US 6,419,682 B1
(45) Date of Patent: Jul. 16, 2002

(54) HEMOSTATIC CLIP CARTRIDGE

(76) Inventors: Timothy Appleby, 105 Willesden Dr., Cary, NC (US) 27513; Matthew Rowland Shute, 3109 Carovel Ct., Raleigh, NC (US) 27612

( * ) Notice: Subject to any disclaimer, the term of this patent is extended or adjusted under 35 U.S.C. 154(b) by 0 days.

(21) Appl. No.: 09/534,683

(22) Filed: Mar. 24, 2000

(51) Int. Cl.[7] .............................................. A61B 17/08

(52) U.S. Cl. ...................................... 606/157; 206/339

(58) Field of Search ................................ 606/151, 157, 606/158, 219, 220, 221, 75; 206/339, 340, 341, 63.3

(56) References Cited

U.S. PATENT DOCUMENTS

| | | | | |
|---|---|---|---|---|
| 4,294,355 A | * | 10/1981 | Jewusiak et al. | 206/339 |
| 4,361,229 A | * | 11/1982 | Mericle | 206/339 |
| 4,936,447 A | * | 6/1990 | Peiffer | 206/339 |
| 5,046,611 A | * | 9/1991 | Oh | 206/339 |
| 5,335,775 A | * | 8/1994 | Scanlon et al. | 206/63.3 |

* cited by examiner

Primary Examiner—David O. Reip
Assistant Examiner—Julian W. Woo
(74) Attorney, Agent, or Firm—Mills Law Firm PLLC

(57) ABSTRACT

A hemostatic clip cartridge for holding a dispensing a polymeric hemostatic clip having a pair of legs connected at proximal ends to a hinge and latching means at distal ends of the legs, and including laterally projecting engagement means adapted to be slidingly received by notched jaws of an applier instrument. The cartridge includes a base having a plurality of longitudinally spaced clip retaining compartments for retaining individual clips carried at the hinge on a saddle extending between adjacent upwardly extending walls. A retainer secured to the base has laterally spaced deflectable arms projecting inwardly toward the saddle in resilient engagement with the legs of the clips. The deflectable arms have a U-shaped medial notch at the distal end having a base wall engagable with the legs and defining laterally spaced terminal fingers registering with said engagement means. For withdrawal the arms are downwardly deflected by an applier instrument with said base wall while maintaining contact with the legs until the fingers contact said engagement bosses. Thereafter, the fingers maintain contact with the bosses until contacted by said applier instrument whereupon further insertion of the applier instrument deflects the arms deflect outwardly and below said engagement means whereby continuous contact is maintained with said clip until affirmative alignment with the jaws of the applier instrument is attained.

5 Claims, 9 Drawing Sheets

HEMOSTATIC CLIP CARTRIDGE

FIELD OF THE INVENTION

The present invention relates surgical clips for ligating or clamping vessels and ducts during surgical procedures and, in particular, a cartridge for holding and dispensing hemostat clips for surgical use.

BACKGROUND OF THE INVENTION

Hemostatic clips are commonly employed in surgical procedures wherein it is desired to ligate or clamp a vessel or duct during surgery. Generally such clips are small metallic or polymeric two-legged configurations that are gripped by a custom applier and closed over the vessel. For metallic clips, the clip permanently deforms at a connecting hinge to establish a locked position. Polymeric clips, on the other hand, require latching configurations or supplemental suturing for maintaining a secure condition.

Inasmuch as the clips are extremely small and lightweight, various holders or cartridges have been proposed for holding an inventory of clips in aligned relation for ready retrieval by the surgeon at time of use. While a distinct improvement from individually selecting clips in bulk, many of the cartridges have significant drawbacks in ease of use, secure withdrawal and convenient access to the cartridge at the surgical arena. Most approaches have focused on symmetrical designs and are not well adapted for more complicated, non-symmetrical designs typical of polymeric latching clips.

For example, the clip cartridge disclosed in U.S. Pat. No. 3,326,216 to Wood provides a series of longitudinally spaced compartments having a central post adapted to compressively engage the inner surface of a two-legged V-shaped metallic clip. The width of the compartment was greater than the clip to enable a clip applier instrument, contoured to the outer periphery of the clip, to capture the clip for withdrawal therefrom. However, normal variations in manufacture of the clips, cartridges, and appliers resulted in conditions wherein the clips were not securely retained and dislodged from the cartridge, shifted in the compartment preventing removal by the applier, or interfered with insertion of the applier for removal. Moreover, the direct abrasive engagement between the applier and the cartridge resulted in abraded particulate material being carried to and deposited at the surgical site, with a consequent possibility of contamination and infection.

To overcome some the above limitations, hemostat clip cartridges have been proposed wherein the clip compartment walls are configured to compressively grip the sides of the clip for the purposes of centering the clip with respect to the applier and preventing dislodging before use. For example, U.S. Pat. No. 4,076,120 to Carroll et al. discloses a cartridge wherein tapered side walls engage and position the clip. For withdrawal, the applier is inserted into the clip compartment to deflect the side walls and permit withdrawal of the clip. However, considerable resistance to removal of the applier is created, requiring excessive withdrawal forces and requiring secure mounting of the cartridge at the surgical arena, using a variety of mechanical clamping devices. Abrasion and contamination problems were also not eliminated. To reduce withdrawal forces, side wall contact was reduced by limiting clip engagement with thin vertical ribs as disclosed in U.S. Pat. No. 4,696,393 to Samuels. Sufficient resistance was nonetheless present to require secure mounting on the cartridge for removal. Abrasion and contamination problems were not eliminated.

In another approach as disclosed in U.S. Pat. No. 4,961,499 to Kulp, it was proposed to slidingly fit a symmetrically legged clip over a conformal center post in the compartment and prevent inadvertent clip dislodgment by disposing projections above and partially overlapping the clip. During removal, the clip directly engaged the projections to deflect the side walls sufficiently to allow clip removal. Nonetheless, considerable resistance to removal remained. Moreover, the conformal support post required that the applicator be accurately aligned with the clip for removal, increasing the dexterity and time of the procedure.

In U.S. Pat. No. 4,936,447 to Peiffer, asymmetrical clips are retained in a cartridge by means of lateral interference at the side walls and by pairs of deflectable fingers that center the clip until the applier makes contact with the clip legs. As the applier makes further contact, the legs are deflected downwardly and do not interfere with clip withdrawal. During the majority of the insertion the applier is in direct contact with the clip with the resultant possibility of abrasion at the applier clip interface. Moreover, the disposition of the fingers are such that the fingers loose contact with the clip prior to the full seating with the applier. Accordingly, the clip may not be securely retained on the applier. Further, the clip support does not accommodate pivoting of the clip for alignment with the applier and as such is not well suited for asymmetrical latching clips.

Inasmuch as the asymmetrical clips have additional criteria for withdrawal, it was proposed in U.S. Pat. No. 5,201,416 to Taylor to mount the latching clip on a saddle that allowed the clip to rotate and thereby assisting in aligning the clip removal bosses with the applier. However, engagement protuberances on the compartment walls need to be deflected to remove the clips such that secure mounting at the surgical arena was necessary. Moreover, the applier jaws were positioned and guided by vertical ledges adjacent the saddle. Normal manufacturing variances in the cartridge and the applier often interacted to create interference conditions potentially contributing to abrasions. Further, the need for accurate jaw alignment necessitated dexterity for both engagement and withdrawal.

A further approach regarding latchable clips in disclosed in U.S. Pat. No. 4,361,229 to Mericle wherein a latchable polymeric clip is pivotally supported on a center post and positioned by deflectable inwardly projecting paper fingers. For removal, the applier initially deflects the fingers and subsequently captures the engagement bosses. However, prior to engagement, the alignment fingers lost contact with the clip such that the clip could assume an unbalanced position requiring substantial force and manipulation to effect seating.

In view of the foregoing, it would be desirable to provide a cartridge for holding and dispensing surgical clips wherein the cartridge could be conveniently and securely mounted, flexibly aligned for clip engagement and withdrawn with minimal resistance.

Accordingly, it is an object of the present invention to provide a surgical clip cartridge that can be conveniently and quickly mounted at the surgical arena.

A further object of the invention is to provide a hemostat clip cartridge presenting minimal resistance to clip withdrawal.

Another object of the invention is to provide a cartridge for surgical clips requiring less exacting alignment of the clip applier for effecting withdrawal of the clip.

Yet another object of the invention is to provide a cartridge for asymmetrical latchable polymeric clips wherein the potential for abrasive contact between the clip applier and the clip is minimized.

Still another object of the invention is to provide a hemostat clip cartridge wherein the clips may be flexibly retained for reception by an applier instrument.

BRIEF SUMMARY OF THE INVENTION

In accomplishing the foregoing objects, the present invention provides hemostatic clip cartridge for holding and dispensing latchable polymeric hemostatic clips characterized by a pair of legs connected at proximal ends to a hinge and latching means at distal ends of the legs. The legs include including projecting engagement bosses adapted to be slidingly received by notched jaws of an applier instrument. The clips are freely supported on vertical saddles in a plurality of clip compartments that accommodate limited sliding and pivotal movement for orientation with an applier instrument. The clips are flexibly preloaded against the saddles by a pair of notched flexible arms. The arms include a distal notch presenting a low friction base surface for engaging the clip legs to provide balanced biasing on the saddles and laterally spaced fingers maintaining transverse clip orientation. The flexible suspension of the clip provides an expanded insertion alignment zone. As the applier is inserted, the arms deflect while maintaining contact with the clip contours and preventing direct contact with the applier and the clip. Thereafter, the fingers contact the bosses and downwardly deflect allowing the clip jaws to securely seat the seat bosses having avoided significant contact with the softer clip material. Thereafter, the loaded applier may be withdrawn without encountering frictional or mechanical resistance, allowing the cartridge to be mounted without mechanical devices using double-faced adhesive tape.

DESCRIPTION OF THE DRAWINGS

The above and other objects and advantages of the present invention will become apparent upon reading the following detailed description of the preferred embodiments taken in conjunction with the accompanying drawings in which.

DETAILED DESCRIPTION OF THE PREFERRED EMBODIMENTS

Figure 1:
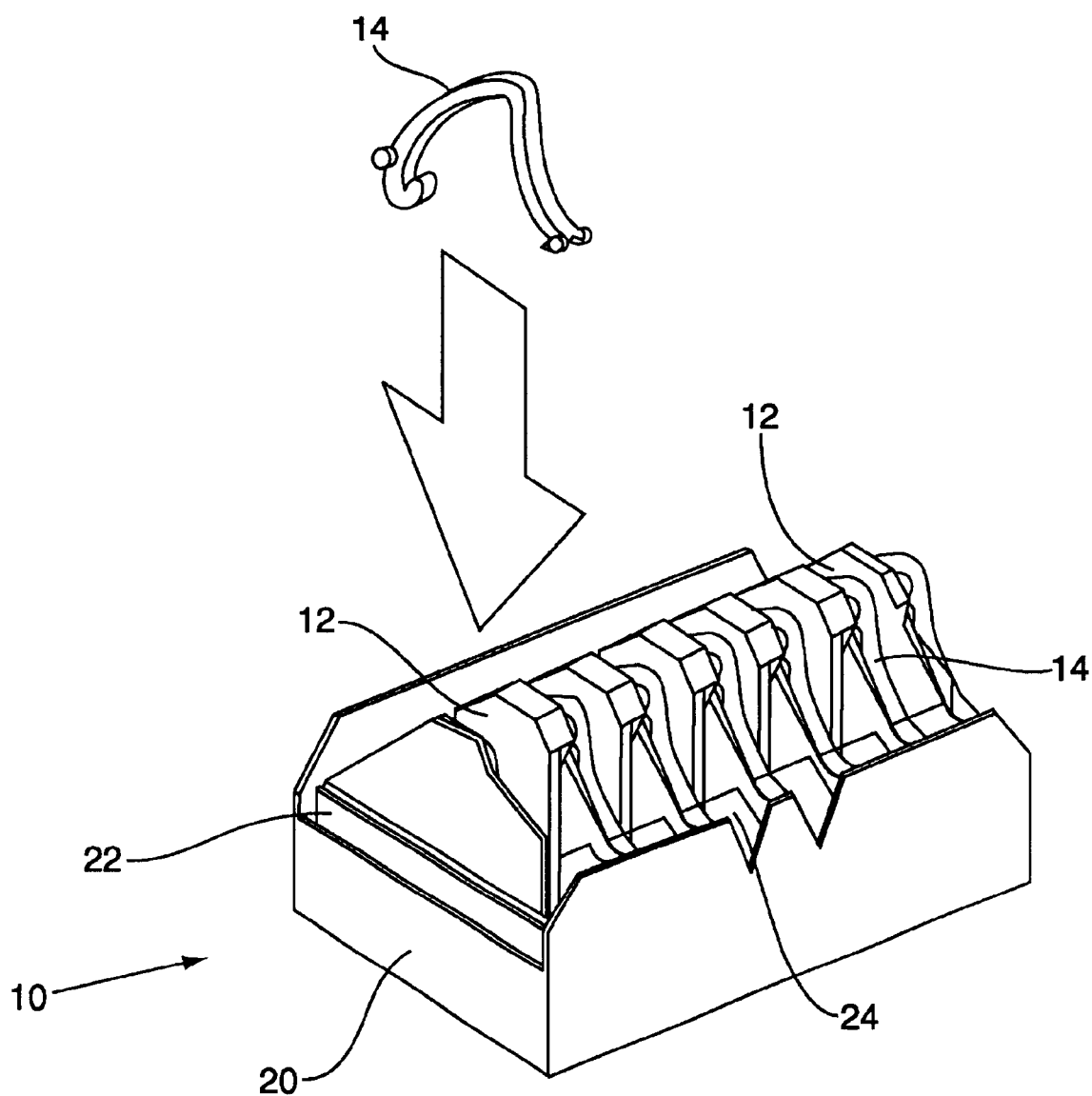
FIG. 1 is a perspective view of a hemostatic clip cartridge in accordance with the present invention.

Referring to the drawings for the purpose of illustrating a preferred embodiment of the present invention and not for limiting same, FIG. 1 shows a cartridge 10 having a longitudinally series of clip compartments 12 into which a latching polymeric hemostatic clip 14 is inserted in the direction indicated by the arrow. The cartridge 10 comprises a rectangular base 20 and a retainer 22. Each of the compartments 12 holds a single clip 14 and is configured as described below to permit an applicator to be inserted for withdrawing the clip 14. The individual clips 14 are retained within the compartments by pairs of opposed transverse retaining fingers 24 on the retainer 22.

The cartridge 10 is particularly well adapted for holding latching polymeric clips of the type disclosed in U.S. Pat. No. 4,834,096 to Oh et al. and will be described with reference thereto. However, it will be appreciated that the features and benefits of the invention may be utilized with respect to symmetrical, metallic and similar surgical clips, wherein convenient storage, access, removal and transfer are desirable.

Figure 2:
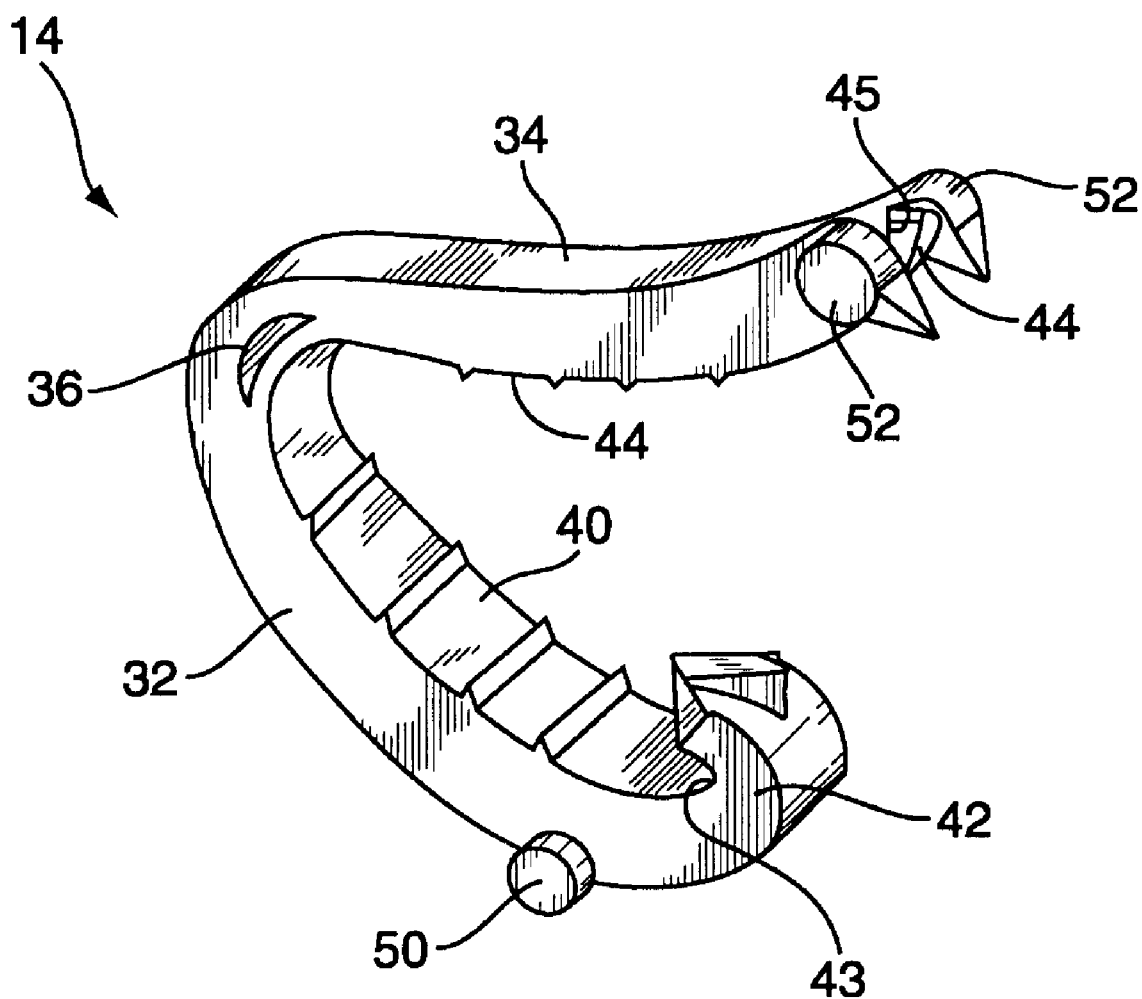
FIG. 2 is an enlarged perspective view of the clip.

For purposes of illustration and as shown in FIG. 2, the clip comprises a first curved leg 32 and a second curved leg 34 joined at their proximal ends by an integral hinge 36. The first leg 32 has a concave inner surface 40 and a curved hook 42 joined at its distal end and defining a rearwardly opening recess 43. The inner surface 44 of the second leg 34 is convex and is adapted to be substantially parallel and complementary to the concave inner surface 40 in the closed position. The hook 42 is curved toward the distal end of the second leg member 34. The distal end 45 of the second leg 34 is beveled and terminates with a tip 44. In the closed position, the tip 44 is received in the recess 43 to lock the leg members in place with the surfaces 40 and 44 in juxtaposition about a vessel to be clamped, all as described in greater detail in the above patent.

Figure 9:
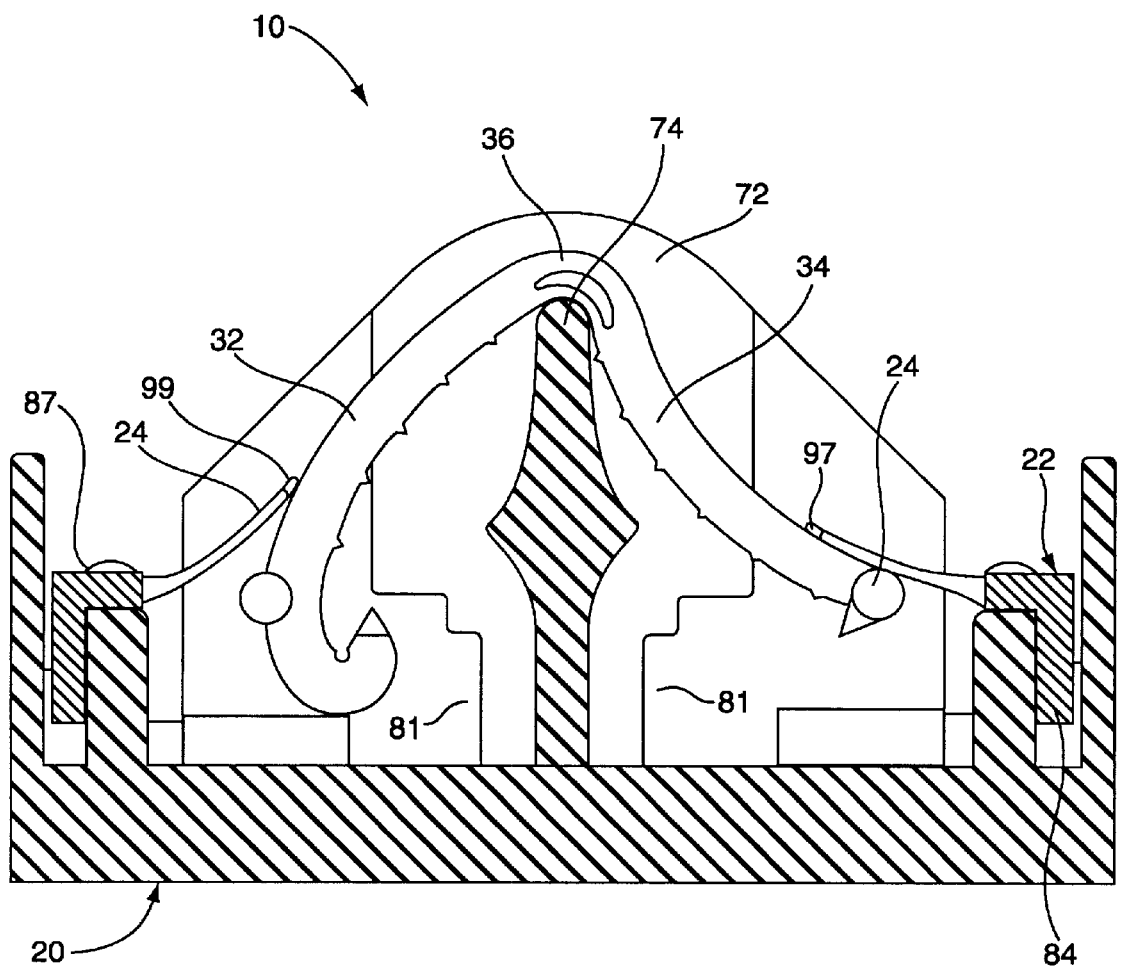
FIG. 9 is a transverse cross sectional view of the cartridge illustrating the retainer arms engaging the clip in the loaded condition.
Figure 10:
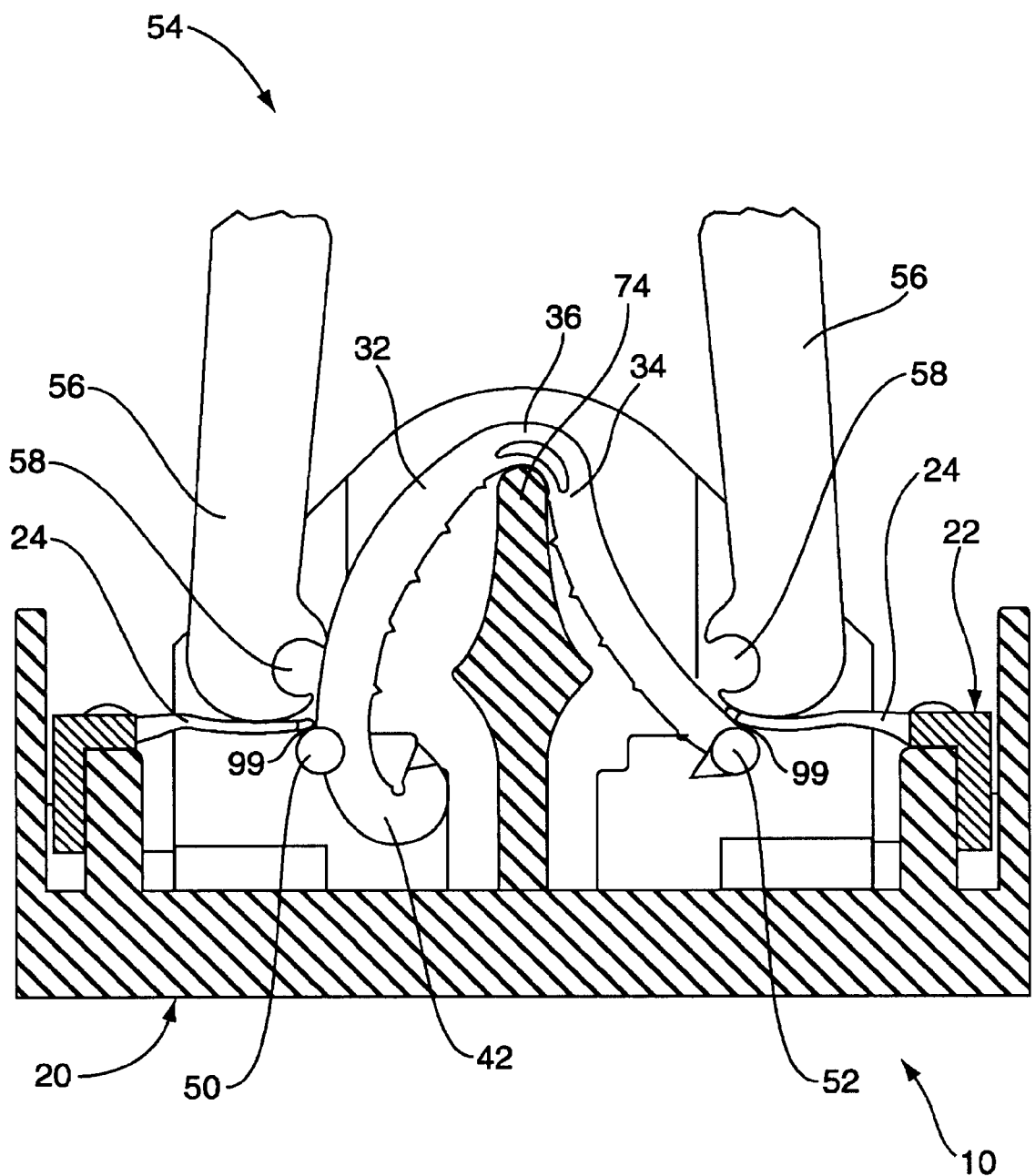
FIG. 10 is a view similar to FIG. 9 illustrating the applier jaws prior to engaging the clip bosses.
Figure 11:
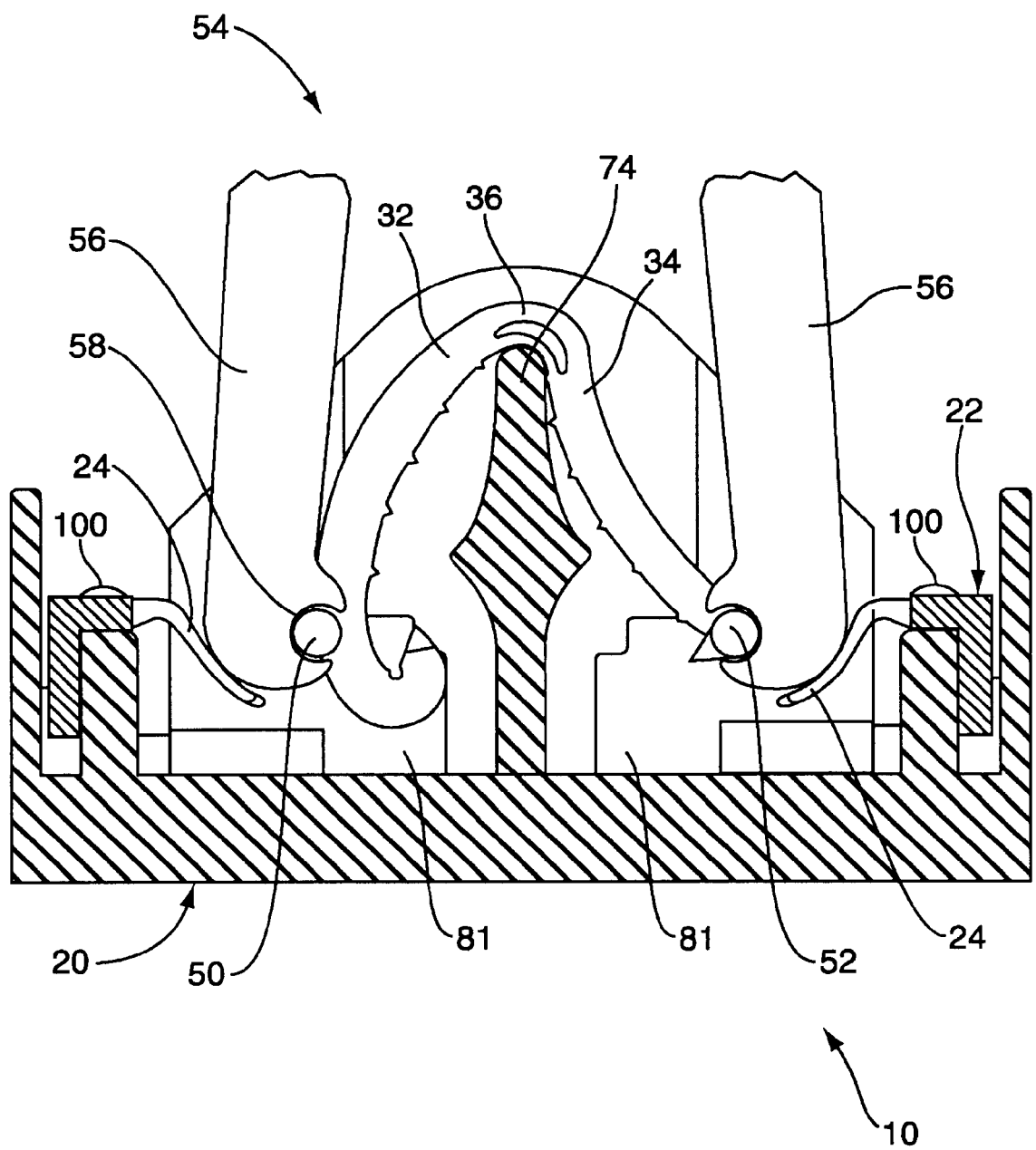
FIG. 11 is a view similar to FIG. 9 illustrating the applier jaws engaging the clip bosses for removal of the clip.

The leg 32 includes a pair of coaxial cylindrical bosses 50 on opposite sides of the hook 42. The leg 34 includes a pair of cylindrical bosses 52 on opposite sides thereof adjacent the tip 44. Referring to FIGS. 9 through 11, a forceps type clip applier 54 including pivotally connected clip jaws 56 is used to remove the clip 14 from the cartridge 10 for transport to the surgical site. Each jaw 56 includes an inwardly opening cutout 58 having a generally circular seating surface for receiving and seating the bosses 50, 52 of the clips for removal from the cartridge 10. The jaws may also be incorporated into conventional endoscopic appliers. Each such applier has a normally open jaw position nominally sized for engaging the clips at the cartridge. Inasmuch as the applier components and cartridge components are subject to manufacturing variation and wear, conditions can exist in prior approaches presenting abrasive conditions creating particulate contaminants that could be carried to the surgical site, or insufficient engagement with the clip for proper withdrawal. Moreover, the prior clips are relatively fixedly disposed requiring precise alignment between the applier jaws and the clip contours. The present invention provides an enlarged insertion zone for the applier overcoming the above limitations and, in combination with the freedom of clip movement during insertion, accommodates flexible alignment of the jaws for engagement and withdrawal.

Figure 3:
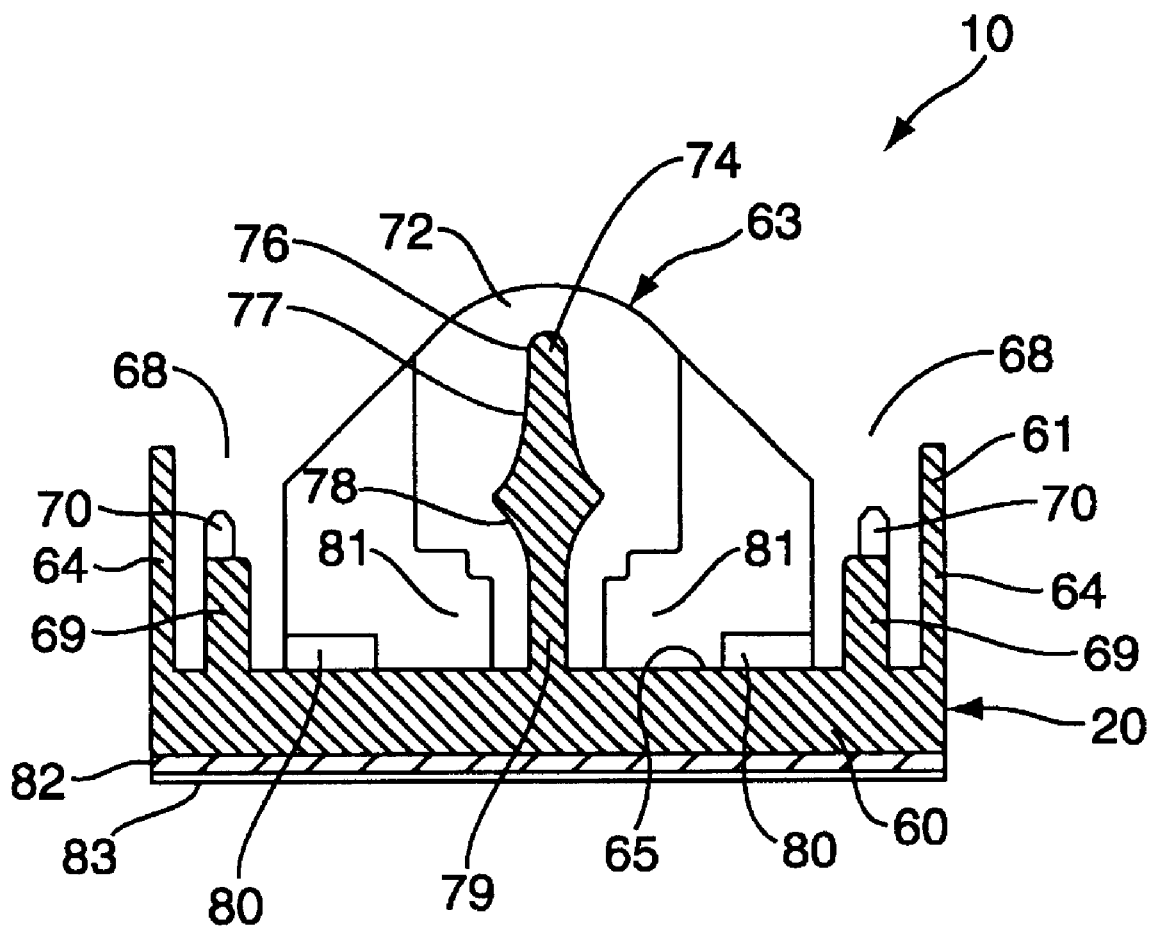
FIG. 3 is a transverse cross sectional view through a clip compartment of the base of the cartridge.
Figure 4:
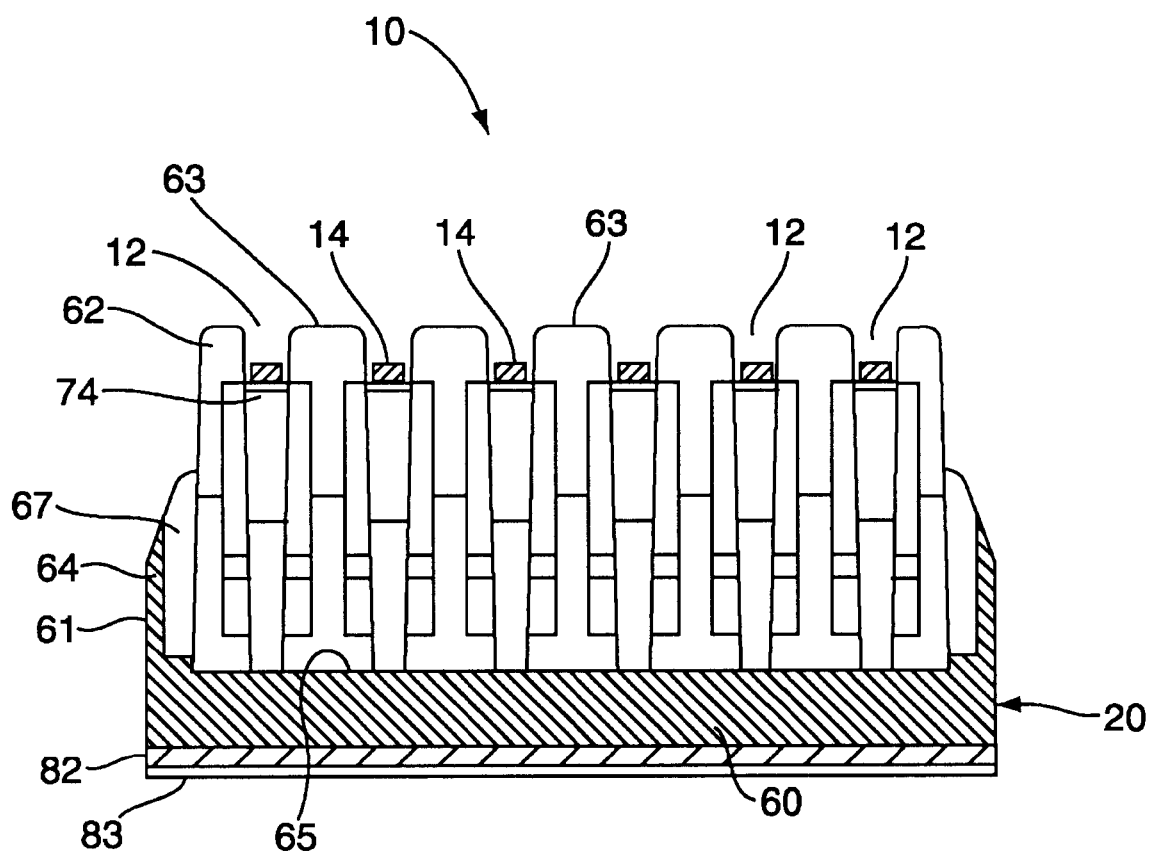
FIG. 4 is a longitudinal cross sectional view of the base of the cartridge illustrating the clip saddle and the transverse position of the clips.

More particularly and as shown in FIGS. 3 and 4, the base 20 is a one piece plastic molding and is symmetrical about a longitudinal central vertical plane. The base 20 comprises a base section 60, a peripheral rim 61 extending above the base section 60, a pair of upwardly extending end walls 62, and a longitudinal series of inner walls 63 uniformly spaced between the end walls 62. As described in greater detail below, the walls 63 and 62 define the clip receiving compartments 12 for the clips 14. The rim 61 includes lateral shoulders 64 extending above the top surface 65 of the base 60 approximately to below the midpoint of the walls 62, 63. The rim 61 includes end shoulder 66 extending slightly above the top surface 65 of the base 60. The end walls 62 are spaced longitudinally inwardly of the end shoulder 66 to establish transverse grooves 67 therebetween. The sides of the walls 62, 63 are spaced laterally inwardly of the side shoulders 64 to define relatively wide longitudinal grooves 68. Longitudinally upwardly extending pedestals 69 are centrally formed in the grooves 68. The outer portions of the groove 68 and the grooves 67 form a peripheral channel for receiving the rim 61 of the retainer 22. Additionally, each pedestal 69 includes a pair of upwardly extending cylindrical posts 70 for locating the retainer 22 in assembly.

Figure 5:
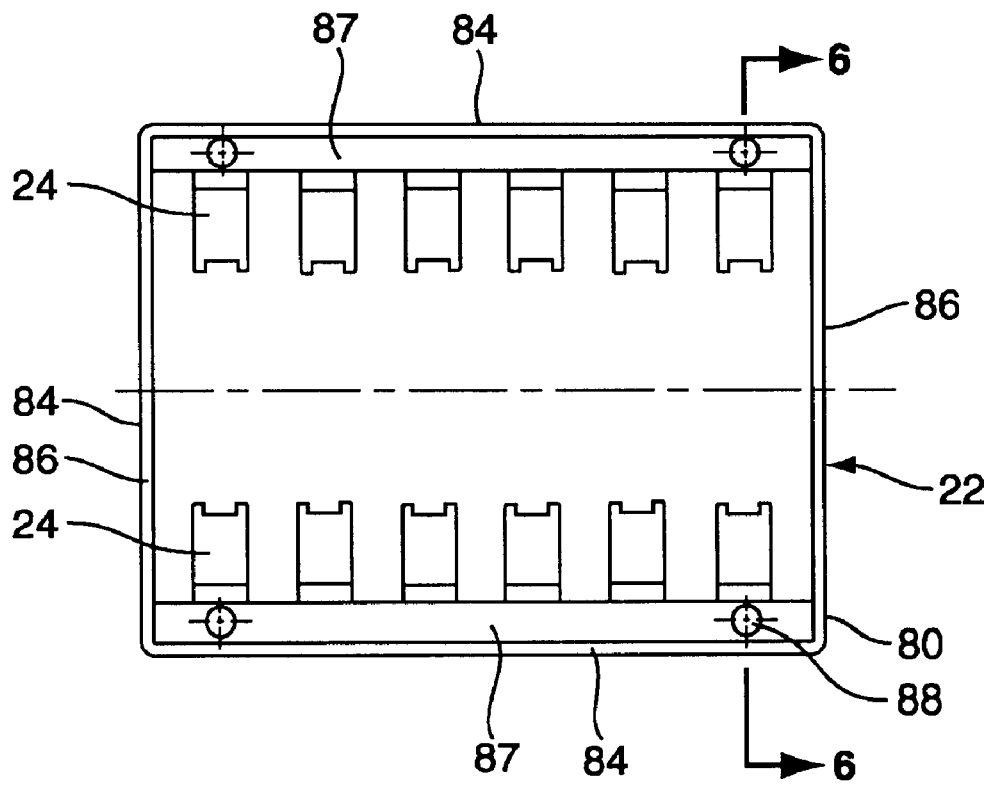
FIG. 5 is a bottom view of the retainer for the cartridge.

As shown in greater detail in FIG. 5, the opposed side walls of each compartment are similar in detail. Each side wall 70 includes a central face 72 symmetrically disposed about the vertical median plane and a longitudinal clip saddle 74 extending therebetween. The central face 72 projects slightly inwardly to establish with the corresponding central face on the opposed wall a vertically opening slot 75 having a width greater than the width of the clip 14 whereby the later may be received loosely therewithin and accommodate limited yaw and longitudinal translation for ready alignment with the applier jaws for engagement and withdrawal, thereby overcoming the need for precise alignment. The saddle 74 includes a rounded upper tip 76 flaring downwardly and outwardly with concave surfaces 77 terminating at the sides of the central face 72 and merging with downwardly and inwardly concave surfaces 78. At about the height of the pedestals 69, the surfaces 78 merge with a lower base panel 79 having a transverse width substantially smaller than the central face 62. A pair of stop blocks extend upwardly from the base section 62 for limiting downward movement of the applier when contacted by the bosses 50, 52 and the arms 24. A pair of laterally outwardly opening stepped notches 81 are formed in the central face 72 below the surfaces 78. The notches 81 accommodate inward flexing and pivoting of the clip bosses 50, 52. A double sided adhesive tape 82 is secured to the lower surface of the base section 60. The tape 82 has a removable outer layer 83 to permit secure mounting of the cartridge at the surgical arena.

Figure 6:
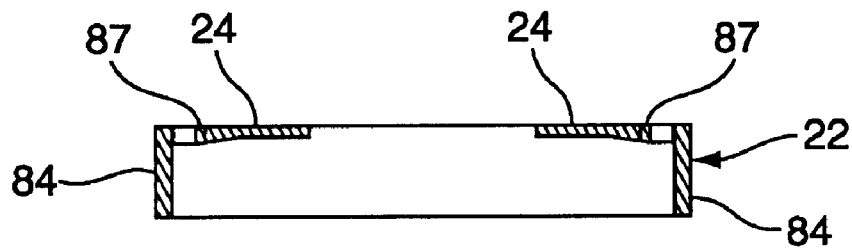
FIG. 6 is a cross sectional view taken along 6—6 in FIG. 5.
Figure 7:
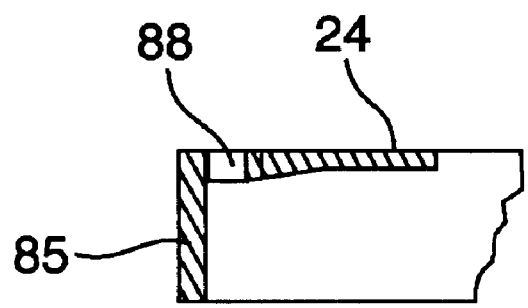
FIG. 7 is an enlarged fragmentary cross sectional view of the retainer.
Figure 8:
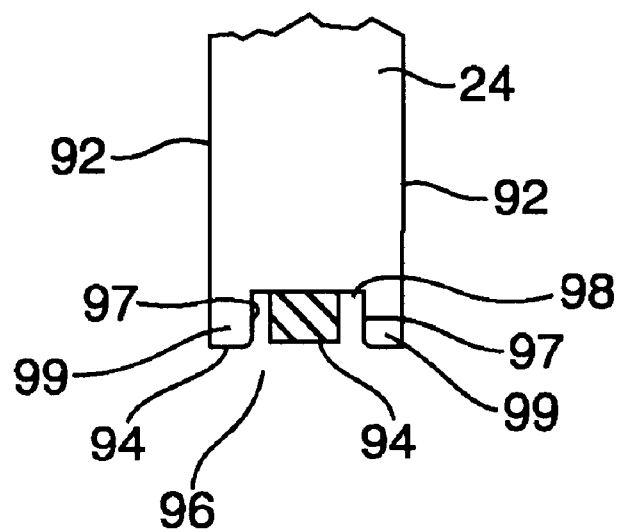
FIG. 8 is an enlarged fragmentary top view of the arms of the retainer shown in FIG. 5.

Referring to FIGS. 5 and 6, the retainer 22 is a one-piece plastic molding formed of a suitable low density, low friction material such as polyethylene. The retainer 22 comprises a peripheral rim 84 having side walls 85 and end walls 86. A pair of laterally spaced longitudinally extending shoulders 87 are formed at the upper ends of the side walls 85 and extend inwardly thereof. The shoulders 87 include spaced openings 88 at the ends thereof registering with the posts 70 on the base 20. In assembly, the side walls 85 are received in the longitudinal grooves 68 exterior of the pedestals 69. The end walls 86 are received in the transverse grooves 67. The ends of the posts 70 are heat staked, ultrasound staked or secured by other suitable means. The longitudinal series of inwardly extending flexible arms 24 are cantilevered at the shoulders 87 and are received in opposed paired relation in the clip compartments 12. The arms 24 are thinner that the shoulders 87 and defined by lateral walls 92 and front wall 94. The arms 24 as formed lie in a common horizontal plane inwardly of the shoulders. The front wall 94 includes a medial cutout 96 having side surfaces 97 and base surface 98. The cut out 96 forms a pair of projecting distal fingers 99. The width of the arms 24 is substantially less than the width of the compartments. The arms are symmetrically disposed within the compartments. The width of the cutout 96 is greater than the transverse width of the clip 14. The fingers 99 are spaced to register with and vertically overlie the bosses 50, 52 on the legs of the clip. The fingers 99 inwardly terminate at the side ledges of the center face of the clip compartment. Accordingly, notwithstanding the loose fit of the clip on the saddle, the arms and the fingers are effective for centering the clip leg members and the bosses in the compartment. Further, as shown in FIG. 9, in assembly the arms 24 engage the clip legs and are initially deflected upwardly thereby providing affirmative biasing against the saddle for orienting the clip despite the asymmetry of the clip legs. Such freedom of clip movement reduces the required insertion accuracy of the applier orientation with respect to the compartment and the clip.

More particularly and as shown in FIGS. 9 through 11, in assembly the clips 14 are loaded in the compartments 12. Thereafter the retainer 22 is inserted into the base 20 and the posts staked to form head sections 100 for securing the components. In the loaded condition of FIG. 9, the arms 24 are upwardly deflected providing a preloading on the arms 32, 34. In this condition the legs assume substantially the as-molded shape and the transverse width therebetween places the bosses 50, 52 outwardly of the notches 81 and beyond the vertical edges of the central face 72. After assembly, the cartridge may be appropriately packaged and sterilized. At the surgical arena, the cartridge may be mounted on any suitable surface, such as a tray or the wrist of the surgeon by removing the protective layer on the adhesive tape and engaging the desired mounting site. As will be hereinafter apparent, the absence of withdrawal resistance make such adaptability possible.

In use, the applier is inserted into the compartment and engages the midportion of the arms 24. Downward movement, the applier jaws cause the arms 24 to downwardly traverse the clip legs 32, 34. During such travel, only the base of the cutout engages the legs and the fingers 99 provide lateral restraint. Affirmative contact is maintained notwithstanding the asymmetry of the legs or pivoting of the clip about the hinge-saddle interface. During such travel, the legs pivot inwardly about the hinge 36 and the hook 42 enters the notch 81. Thereafter as shown in FIG. 10, the fingers 99 engage the bosses 50, 52 while the arms 24 continue to isolate the hard metallic surfaces of the applier jaws from the softer, less abrasive resistant clip material. At this stage, the jaws cause the legs to centrally flex and the fingers to progressively traverse the contours of the bosses. Only after the fingers have outwardly cleared the bosses do the jaws of the applier physically engage the clip. Further downward movement of the jaws springs the arms below the bosses and allows the bosses to seat in the cutouts 58 of the applier jaws 56. In this condition, it will be appreciated that withdrawal of the applier and carried clip is not resisted, mechanically or frictionally, by engagement with the cartridge. Accordingly, the clip may be withdrawn without any tensile loading at the adhesive mounting interface. Further, the path of withdrawal has substantial freedom of movement without incurring frictional or abrasive interference.

While the present invention has been described with reference to an asymmetrical design with lateral engagement and retraction means, it will be appreciated that flexible, low resistance features may be afforded to other designs including symmetrical designs, deformable clips, and non-projecting engagement surfaces.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the sprit and scope of the present invention. The disclosures and description herein are intended to be illustrative and are not in any sense limiting of the invention, which is defined solely in accordance with the following claims.

What is claimed:

1. A hemostatic clip cartridge, comprising: a latchable polymeric hemostatic clip having a pair of asymmetric legs connected at proximal ends to a hinge and having latching means at distal ends, said legs having laterally projecting bosses on the sides thereof; a clip base having a clip retaining compartment defined by a pair of upwardly extending walls laterally spaced at a distance greater than the lateral width of the legs and slidably receiving said clip; a saddle laterally extending between said walls engaging a lower surface of said hinge and accommodating pivotal and lateral movement of said clip; adhesive means carried on a lower surface of said clip base for attachment to a mounting surface; a retainer secured to said base having transversely opposed inwardly projecting flexible arms, said arms having a medial notch at the distal end defined by a base wall and laterally spaced, inwardly extending fingers, said base wall normally engaging and upwardly deflected by said the legs in a normal storage condition with said fingers on opposed sides of each of said legs and aligned with surfaces of said projecting bosses.

2. The clip cartridge as recited in claim 1 wherein said retainer is formed of a low density, low friction material.

3. The clip cartridge as recited in claim 2 wherein said material is polyethylene.

4. The clip cartridge as recited in claim 1 wherein said arms are of a uniform width.

5. In combination with an applier instrument having a pair of notched jaws, a hemostatic clip cartridge comprising: a plurality of polymeric hemostatic clips, each of said clips having a pair of asymmetric legs connected at proximal ends to a hinge and having latching means at distal ends, said distal ends of said clips including laterally projecting engagement means received by said notched jaws in a retrieval condition; a base having a plurality of laterally spaced clip retaining compartments, each compartment defined by a pair of upwardly extending walls having a width greater than the lateral width of said legs of the clip and slidably receiving a clip therewithin; a saddle laterally extending between said walls for supporting the hinge of the clip and accommodating pivotal and lateral movement of said clip; a retainer secured to said base, said retainer having laterally spaced deflectable arms projecting inwardly toward said saddle, said arms having a medial notch at the distal end, said notch having a base wall bounded by a pair of inwardly extending fingers, said base wall compressively engaging and upwardly deflected by said legs in a storage condition with said fingers aligned with said engagement means, said base wall extending parallel to a longitudinal axis of said base and having a width greater than a width of said legs, said arms being downwardly deflected against said legs by said applier instrument during movement from said normal condition to said retrieval condition with said base wall maintaining contact with said legs until said fingers contact said engagement means, said fingers maintaining contact with said engagement means until contacted by said applier instrument, and upon further inserting movement of said applier instrument to said retrieval condition, deflecting outwardly and below said engagement means whereby continuous contact is maintained with said clip until said engagement means is engaged by said notched jaws of the applier instrument.

* * * * *